United States Patent
Lee et al.

(10) Patent No.: US 7,399,716 B2
(45) Date of Patent: Jul. 15, 2008

(54) PRECURSOR FOR HAFNIUM OXIDE LAYER AND METHOD FOR FORMING HAFNIUM OXIDE FILM USING THE PRECURSOR

(75) Inventors: Jung-hyun Lee, Suwon (KR); Yo-sep Min, Suwon (KR); Young-jin Cho, Incheon (KR)

(73) Assignee: Samsung Electronics Co., Ltd., Suwon, Kyungki-Do (KR)

( * ) Notice: Subject to any disclaimer, the term of this patent is extended or adjusted under 35 U.S.C. 154(b) by 359 days.

(21) Appl. No.: 11/340,692

(22) Filed: Jan. 27, 2006

(65) Prior Publication Data

US 2006/0118891 A1    Jun. 8, 2006

Related U.S. Application Data

(62) Division of application No. 10/638,329, filed on Aug. 12, 2003, now Pat. No. 7,030,450.

(30) Foreign Application Priority Data

Aug. 12, 2002 (KR) ............................ 2002-0047518

(51) Int. Cl.
*H01L 21/44* (2006.01)
(52) U.S. Cl. .................. 438/785; 438/680; 257/E21.09
(58) Field of Classification Search .................. 438/680, 438/785
See application file for complete search history.

(56) References Cited

U.S. PATENT DOCUMENTS

| 5,486,712 | A | 1/1996 | Arima |
| 6,348,386 | B1 * | 2/2002 | Gilmer .................. 438/288 |
| 6,420,279 | B1 | 7/2002 | Ono et al. |
| 7,030,450 | B2 * | 4/2006 | Lee et al. .............. 257/411 |
| 2002/0084471 | A1 | 7/2002 | Won et al. |
| 2003/0054615 | A1 | 3/2003 | Kim et al. |
| 2003/0227033 | A1 | 12/2003 | Ahn et al. |
| 2004/0065938 | A1 | 4/2004 | Won et al. |
| 2004/0209765 | A1 | 10/2004 | Boussie et al. |

FOREIGN PATENT DOCUMENTS

| JP | 2002/060944 | 2/2002 |
| KR | P2001-0090005 | 10/2001 |
| KR | P2001-0098415 | 11/2001 |
| KR | P2002-0001337 | 1/2002 |
| WO | 98/57975 | 12/1998 |

OTHER PUBLICATIONS

Akimasa Yajima et al., "Formation Process of Hafnium Nitride by the Reaction of Hafnium Tetrachloride with Ammonia in the Vapor Phase and Properties of the Hafnium Nitride Formed", Res. Lab Resourc. Util., Tokyo Inst Technol., Yokohama, Japan, 1986 vol. 9, p. 1175-80.

(Continued)

*Primary Examiner*—Alexander G Ghyka
(74) *Attorney, Agent, or Firm*—Buchanan Ingersoll & Rooney PC

(57) ABSTRACT

A hafnium oxide precursor and a method for forming a hafnium oxide layer using the precursor are provided. The hafnium oxide precursor contains a nitrogen compound bound to $HfCl_4$.

7 Claims, 5 Drawing Sheets

OTHER PUBLICATIONS

G.M. Toptygina et al., "Alcoholysis of Zirconium and Hafnium Tetrachloride in the Presence of Pyridine", Inst. Obshch. Neorg. Khim. Im. Kurnakova, Moscow, USSR Zhurnal Neorganicheskoi Khimii, 1972, 14(8), p. 2119-22.

G.M. Toptygina et al., "Hydrolysis of Zirconium and Hafnium Tetrachlorides in the Presence of Pyridine in Carbon Tetrachloride", Zhurnal Neorganicheskoi Khimii, 1971, 16(5), p. 1279-300.

Bruno Crociani et al., "Insertion of Isonitriles into Metal-Halogen Bonds", Journal of Organometallic Chemistry, 1975, p. c1-c3, vol. 101, No. 1, Elsevier Sequoia S.A., Lausanne, Netherlands.

Official Action issued by the Patent Office of the People's Republic of China in corresponding Chinese Patent Application No. 031530850, Apr. 6, 2007; and English translation thereof.

* cited by examiner

PRECURSOR FOR HAFNIUM OXIDE LAYER AND METHOD FOR FORMING HAFNIUM OXIDE FILM USING THE PRECURSOR

BACKGROUND OF THE INVENTION

This application claims the priority of Korean Patent Application No. 2002-47518, filed Aug. 12, 2002 in the Korean Industrial Property Office, which is incorporated herein in its entirety by reference.

1. Field of the Invention

The present invention relates to a precursor for hafnium oxide layer and a method for forming a hafnium oxide layer using the precursor, and more particularly, to a precursor for a hafnium oxide layer that can be deposited at a low temperature and a higher rate with enhanced electrical characteristics and step coverage, a method for forming a hafnium oxide layer using the precursor, a capacitor and a transistor using the hafnium oxide layer formed by the method, and an electronic device using the capacitor and/or transistor.

2. Description of the Related Art

Dielectric materials are used in the formation of gate oxide layers or capacitor dielectric layers of semiconductor (memory) devices. The characteristics of the dielectric materials greatly affect the operational characteristics of the devices. Conventionally, a silicon oxide layer has been widely used as a gate oxide layer or a capacitor dielectric layer. However, as semiconductor devices are more highly integrated, research on a hafnium oxide layer, a zirconium oxide layer, an aluminum oxide layer, and a strontium titanate layer, which have a high dielectric constant, is done. Among those promising dielectric materials, hafnium oxide ($HfO_2$) is expected to be the most useful in next-generation highly integrated semiconductor memory devices because it has a high band gap energy of 5.9 eV and a dielectric constant of 20 or greater, and provides good interfacial stability between silicon and Hf—O.

The hafnium oxide layer can be deposited by a variety of conventional methods, for example, sputtering, chemical vapor deposition (CVD), or atomic layer deposition (ALD). Due to the requirement for excellent step coverage in more highly integrated devices, the ALD method becomes more interesting. However, a desired level of step coverage cannot be satisfied with the ALD method where a thin film of a thickness level of atomic layers is repeatedly deposited.

Also, the rate at which the hafnium oxide layer is deposited is slow. Accordingly, silicon deposited as a lower electrode is oxidized into $SiO_2$ during the deposition of the hafnium oxide layer. As a result, as is widely known, the dielectric characteristics cannot be achieved with only a single $HfO_2$ layer. For example, when a $HfO_2$ layer is deposited using $HfCl_4$, which is most widely used, as a Hf source, the deposition rate of the $HFO_2$ layer is as low as 0.07 nm/cycle, although it is theoretically as high as 0.11 nm/cycle or greater. A reason for the low deposition rate is considered to be due to the repulsive force between adjacent Cl atoms in the molecules, which reduces the amount of the $HfCl_4$ deposited in a unit area.

$HfCl_4$ as a major Hf source is in a solid state at room temperature and has a low vapor pressure of 0.1 torr at 200° C. Accordingly, when a bubbling method is applied, a very small amount of the $HfCl_4$ can be provided into a reactor for each cycle. Therefore, when the Hf source is applied to form a three-dimensional capacitor, surface-area widens too far and poor step coverage is inevitable.

SUMMARY OF THE INVENTION

Accordingly, the present invention provides a precursor for hafnium oxide layer without the problems of the conventional Hf source, $HfCl_4$.

The present invention provides a method for forming a hafnium oxide layer using the precursor for hafnium oxide.

The present invention provides a capacitor or a transistor for memory devices that has a hafnium oxide layer formed by the above method and an electronic device including the capacitor or transistor.

In one aspect, the present invention provides a precursor for hafnium oxide layer containing a nitrogen compound bound to $HfCl_4$. The nitrogen compound includes pyridines, amines, and nitriles.

In another aspect, the present invention provides a method for forming a hafnium oxide layer, comprising: preparing a solution of a precursor for hafnium oxide layer containing a nitrogen compound bound to $HfCl_4$; adsorbing the hafnium oxide layer precursor solution onto a surface of a substrate in a reactor; and oxidizing the product adsorbed on the surface of the substrate by supplying an oxidizing agent into the reactor, to form an atomic hafnium oxide layer on the substrate.

In another aspect, the present invention provides a capacitor structure comprising: a lower electrode; a dielectric layer formed on the lower electrode; and an upper electrode formed on the dielectric layer, wherein the dielectric layer is deposited on the lower electrode by the method described above.

In another aspect, the present invention provides a transistor structure comprising: a source electrode; a drain electrode; a substrate having a conductive region between the source electrode and the drain electrode; a gate dielectric layer formed on the conductive region of the substrate; and a gate electrode formed on the gate dielectric layer, wherein the gate dielectric layer is deposited on the conductive region by the method described above.

In another aspect, the present invention provides an electronic device including at least one of the capacitor structure and the transistor structure formed by the method described above. Preferably, the electronic device is a dynamic random access memory (DRAM) device.

BRIEF DESCRIPTION OF THE DRAWINGS

The above objects and advantages of the present invention will become more apparent by describing in detail exemplary embodiments thereof with reference to the attached drawings in which.

DETAILED DESCRIPTION OF THE INVENTION

According to the present invention, instead of the conventional hafnium precursor, $HfCl_4$, a hafnium oxide layer precursor containing a nitrogen compound coordinated to $HfCl_4$ and acting as a Lewis base is used.

Figure 1:
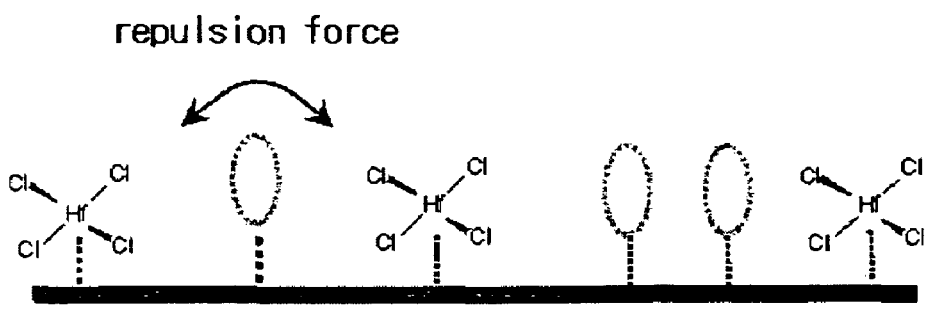
FIG. 1 illustrates the atomic interaction in a conventional hafnium oxide precursor.
Figure 2:
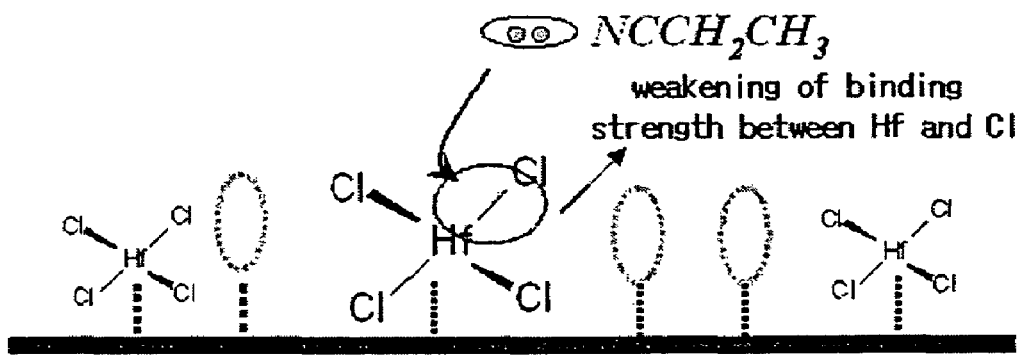
FIG. 2 illustrates the atomic interaction in a hafnium oxide precursor according to the present invention.

As the nitrogen-based compound capable of acting a Lewis base is bound to $HfCl_4$, a free electron pair of the nitrogen compound is provided to the core metal hafnium, as shown in FIG. 2, and the binding force between the hafnium and Cl atoms becomes weak. As a result, when the precursor is adsorbed on a substrate, the repulsion of adjacent Cl atoms and the binding force between the hafnium and Cl atoms are reduced, thereby increasing the rate at which the hafnium is oxidized for each cycle and increasing the amount by which $HfCl_4$ is deposited in a unit area. As a result, the rate at which a hafnium oxide layer is deposited is improved. Due to the improved deposition rate, a period of time during which a lower electrode is exposed under unnecessary oxidization conditions and an oxide is less formed in the lower electrode, thereby resulting in enhanced electrical characteristics.

The donation of the electron pair to the core metal hafnium facilitates interactions between the hafnium and the substrate, and thus enhances the binding force therebetween. In other words, the binding force between the resulting hafnium oxide layer and the substrate is enhanced. In a similar manner, due to the reduced binding force between the core metal hafnium and Cl atoms, the Cl atoms are easily dissociated by an oxidizing agent, so that binding of oxygen to the hafnium is facilitated.

The hafnium oxide precursor according to the present invention can be derived by binding a nitrogen compound capable of acting as a Lewis base to $HfCl_4$. $HfCl_4$ is in a solid state at room temperature. For the binding with the nitrogen compound, it is preferable that $HfCl_4$ be in a liquid state at room temperature. For example, when acetonitrile is used as the nitrogen compound, solid $HfCl_4$ is dispersed in acetonitrile, which is liquid at room temperature, and evaporated in a vacuum. The resulting residue is used as a hafnium oxide layer precursor containing the nitrogen compound bound to $HfCl_4$. Here, $HfCl_4$ is added to the nitrogen compound in a concentration of 0.01-1M.

When a nitrogen compound which is not liquid at room temperature is used, an organic solvent capable of dissolving or diluting the nitrogen compound can be used so as to obtain a hafnium oxide precursor according to the present invention. Suitable organic solvents includes, but not limited to, cyclohexane, tetrahydrofuran, n-butylacerate, butyronitrile, propionitrile, etc. In this case, it is preferable that the concentration of $HfCl_4$ is in the range of 0.01-1M.

Preferably, the nitrogen compound suitable for the hafnium oxide precursor according to the present invention, having an lone electron pair as a Lewis base, is pyridines, amines, or nitriles.

Suitable amines for the nitrogen compound may have formula (1) below:

wherein $R_1$, $R_2$, and $R_3$ are independently hydrogen, halogen atom, and a substituted or unsubstituted $C_1$-$C_{10}$ alkyl group.

Examples of amines suitable for the nitrogen compound include, but not limited to, amine, monomethylamine, monoethylamine, monopropylamine, monoisopropylamine, methylethylamine, methylpropylamine, ethylpropylamine, dimethylamine, diethylamine, dipropylamine, diisoprolylamine, dibutyroamine, etc.

Suitable nitriles for the nitrogen compound may have formula (2) below:

where $R_4$ is a substituted or unsubstituted $C_1$-$C_{10}$ alkyl group. Examples of nitriles for the nitrogen compound include, but not limited to, acetonitrile, isopropylnitrile, butyronitrile, etc.

Suitable pyridines for the nitrogen compound may have formula 3 below:

where $R_5$, $R_6$, $R_7$, $R_8$, and $R_9$ are independently substituted and unsubstituted $C_1$-$C_{10}$ alkyl groups, a cyano group, an amino group, and a hydroxyl group, respectively. Examples of pyridines for the nitrogen compound include, but not limited to, pyridine, ethylpyridine, methylpyridine, propylpyrazine, pyrazole, etc.

Among those substituted groups described above, the substituted or unsubstituted alkyl group means straight and branched chain radicals having from 1 to 10 carbon atoms, and preferably, having from 1 to 8 carbon atoms, and more preferably, having from 1 to 5 carbon atoms. Examples of these radicals include methyl, ethyl, n-propyl, n-butyl, isobutyl, sec-butyl, t-butyl, pentyl, isoamyl, hexyl, octyl, etc. Lower alkyl radicals having from 1 to 3 carbon atoms are most preferred. At least one hydrogen atom in those alkyl groups may be replaced by halogen atom, a hydroxyl group, a carboxyl group, a cyano group, an amino group, etc.

The hafnium oxide layer precursor according to the present invention can be used in forming a multi-layered structure including a hafnium oxide layer or a multi-component layer. The hafnium oxide layer can be formed by general methods, for example, CVD, ALD, etc.

A method for forming a hafnium oxide layer by ALD will be described. Initially, a hafnium oxide layer precursor containing the nitrogen compound bound to $HfCl_4$ according to the present invention is dissolved in or diluted with a predetermined organic solvent to obtain a precursor solution. Since the precursor containing the nitrogen compound bound to $HfCl_4$ is in a solid state, it is desirable to prepare the precursor solution rather than to directly inject the solid precursor into an evaporator, for higher deposition efficiency. For this reason, the hafnium oxide layer precursor is dissolved in or diluted with the organic solvent. Suitable organic solvents include, but not limited to, cyclohexane, tetrahydrofuran, n-butylacerate, butyronitrile, propionitrile, etc. Here, the amount of the added organic solvent is controlled such that the concentration of $HfCl_4$ in the precursor solution is in the range of 0.01-1.0M.

Alternatively, in the preparation of the precursor solution, that nitrogen compound bound to $HfCl_4$ in the solid precursor can be further added in an appropriate amount to enhance the chemical stability of the precursor solution. For example, when a solid precursor obtained by binding acetonitrile and $HfCl_4$ is used, an appropriate amount of the acetonitrile is further added when the solid precursor is dissolved in an organic solvent, to improve chemical stability. Here, the amount of the added nitrogen compound is controlled such that the concentration of $HfCl_4$ in the precursor solution is in the range of 0.01-1.0M.

Next, a substrate on which a thin film will be deposited is heated. The substrate is transferred into a reactor, and the temperature of the substrate is stabilized therein within a predetermined range. Preferably, the temperature of the substrate is in the range of 200-500° C., and more preferably, 250-500° C. If the temperature of the substrate is less than 200° C., physical adsorption of $HfCl_4$ is too excess to be purged. If the temperature of the substrate is greater than 500° C., the precursor decomposes and vaporizes before deposition. As a result, the precursor is deposited by CVD, rather than by ALD.

Any kinds of substrates can be used without limitations. Examples of suitable substrates include a poly-Si substrate, a $TiN/Si$ substrate, a $Ru/SiO_2/Si$ substrate, and a $Pt/Ti/SiO_2/Si$ substrate.

Next, an inert gas is supplied into the reactor to create a non-oxidization environment. Argon gas, nitrogen gas, etc. can be used as the inert gas.

Preferably, the inert gas is flowed at a rate of 30-500 sccm. If the flow rate of the inert gas is beyond this range, the vapor partial pressure of the precursor is lowered, and the rate of deposition of the precursor is reduced.

Next, the hafnium oxide precursor according to the present invention is evaporated using a vaporizer and supplied into a reactor so as to be adsorbed on the surface of the substrate. Preferably, the temperature of the vaporizer is controlled in the range of 180-260° C., and more preferably, 220-240° C., in terms of precursor's stability and vaporization efficiency. Preferably, the precursor is supplied at a flow rate of 0.01-0.3 cc/min. If the temperature of the vaporizer is less than 180° C., part of $HfCl_4$ does not vaporize and remains within the vaporizer, thereby clogging the vaporizer. If the temperature of the vaporizer is greater than 260° C., a portion of $HfCl_4$ is deposited on the wall of the vaporizer.

According to the present invention, the hafnium oxide precursor can be supplied into the vaporizer by a variety of methods without limitations, for example, by using a bubbler or by a direct spraying method.

In the direct spraying method, a solution of the hafnium oxide precursor prepared by dissolving the solid precursor in or diluting it with an organic solvent in an appropriate concentrate is directly supplied into the vaporizer through a nozzle. In the direct spraying method, the precursor is supplied to the vaporizer under time-division synchronization. In particular, the nozzle is opened for a period of time to supply the precursor and then closed to stop supplying the precursor. As a result, the consumption of the precursor is reduced. Alternatively, opening and closing of the nozzle can be repeated several times. Next, the aerozole sprayed through the nozzle is vaporized. As a result, the amount by which the precursor is supplied for each cycle is greatly increased. The drawback of a high boiling point in $HfCl_4$ can be eliminated by supplying the precursor by this method.

After the hafnium oxide layer precursor solution according to the present invention is adsorbed on the surface of the substrate, as described above, the unadsorbed, excess precursor is purged using an inert gas. The rate of flowing the inert gas can be varied according to the deposition equipment. Preferably, the inert gas is flowed at a rate of 100-500 sccm. Preferably, the operating pressure of the reactor is controlled in the range of 0.1-3 torr. The purging process using the inert gas can be omitted as needed.

Next, the hafnium oxide layer precursor, $HfCl_4$ coordinated with the nitrogen compound, adsorbed on the surface of the substrate is oxidized by injection of an oxidizing gas to form a $HfO_2$ layer as an atomic layer. Water vapor, $O_2$ gas, $N_2O$ gas, or plasma-enhanced $O_2$ or $O_3$ gas can be used as the oxidizing gas. The oxidizing gas can be flowed at different rates. However, it is preferable that the oxidizing gas be flowed at a rate of 100-300 sccm.

A reaction activator can be further added before or after supplying the oxidizing agent, or simultaneously. Preferable reaction activators include pyridines, acetonitriles, and amines. The reaction activator makes oxidation of the precursor easier by weakening the Hf—Cl bond during oxidation of the precursor, thereby improving deposition efficiency.

The above-described processes of purging the reactor using an inert gas, adsorbing the hafnium oxide precursor on the substrate, purging excess precursor using an inert gas, and oxidizing the hafnium oxide precursor can be repeatedly performed until a $HfO_2$ layer having a desired thickness is obtained. Preferably, the $HfO_2$ layer has a thickness of 20-200 Å and a dielectric constant of about 25.

The formation of the $HfO_2$ layer may be followed by high-temperature annealing to further crystallize the $HfO_2$ in order to obtain enhanced dielectric characteristics. Preferably, the high-temperature annealing is performed at a temperature of 500-900° C. for 1-30 minutes in an oxidation or vacuum environment. The oxidation environment is created using water vapor, $O_2$ gas, $N_2O$ gas, or plasma-enhanced $O_2$ or $O_3$ gas. Preferably, the degree of vacuum is controlled in the range of about 0.01-10 torr, and more preferably, about 35 mtorr.

Hereinafter, a method for forming a hafnium oxide layer by CVD will be described.

Initially, an oxidation environment is created in a reactor. The oxidation environment can be created using an oxidizing gas, for example, water vapor, $O_2$ gas, $N_2O$ gas, or plasma-enhanced $O_2$ or $O_3$ gas. The rate of flowing the oxidizing gas can be varied according to the deposition equipment. However, it is preferable that the oxidizing gas be flowed at a rate of 100-500 sccm.

Next, the temperature of a substrate on which a hafnium oxide layer will be formed is stabilized with a predetermined range. Preferably, the temperature of the substrate is in the range of 200-500° C. If the temperature of the substrate is beyond this range, the problems described in the ALD method above can occur. The same kinds of substrates as those described in the ALD method above can be used.

The hafnium oxide layer precursor is supplied into the reactor in the oxidation atmosphere to deposit a $HfO_2$ layer on the substrate. The composition of the hafnium oxide precursor, the method of supplying the hafnium oxide precursor, and other conditions can be the same as or similar to those described in the above ALD method.

Similar to the ALD method described above, the formation of the $HfO_2$ layer may be followed by high-temperature annealing under the same conditions described above, in order to facilitate crystallization of the $HfO_2$.

The hafnium oxide precursor according to the present invention can be used in the manufacture of electronic devices. The terms "electronic devices" mean transistors, capacitors, diodes, resistors, switches, light emitting diodes, lasers, or interconnection structures.

As an example, a capacitor has a structure where a dielectric layer is formed between an upper electrode and a lower electrode, wherein the dielectric layer is formed of a HfO$_2$ layer by the method described above. Any material can be used for the upper and lower electrodes without limitations. For example, Si, TiN, and Pt group elements can be used as materials for the upper and lower electrodes. At least one element selected from the Pt group consisting of, for example, ruthenium (Ru), osmium (Os), iridium (Ir), and platinum, can be used.

As an example, a method for manufacturing the capacitor structure will be described. Initially, on the surface of a lower electrode formed of a Pt group element, a HfO$_2$ layer is formed using the hafnium oxide precursor according to the present invention by ALD or CVD.

Next, an upper electrode is formed on the HfO$_2$ layer, followed by high-temperature annealing. As described above, the high-temperature annealing process is performed in order to further crystallize the HfO$_2$ and enhance the dielectric characteristics. Preferably, the high-temperature annealing is performed at a temperature of 500-900° C. for 1-30 minutes in an oxidation, inactive, or vacuum environment. When the high-temperature annealing is performed in a vacuum, the degree of vacuum is controlled in the range of 0.01-10 torr, and preferably, at about 35 mtorr.

The high-temperature annealing may be followed by a supplementary thermal process. The supplementary thermal process is performed when the upper and lower electrodes, which are formed on and underneath the HfO$_2$ dielectric layer, are hardly oxidized, in order to supplement oxygen into the interface between the HfO$_2$ layer and each of the upper and lower electrodes. The supplementary thermal process is performed at less than 1000° C., and preferably, at 450-750° C., for 10-60 minutes in a vacuum, an inactive environment, or in the air.

A hafnium oxide layer according to the present invention can be used in forming a gate dielectric layer of a transistor. In particular, on a conductive region between a source electrode and a drain electrode in a substrate, a HfO$_2$ layer is deposited as a gate dielectric layer by the method as described above. Next, a gate electrode is formed on the gate dielectric layer, thereby resulting in a transistor.

Figure 3:
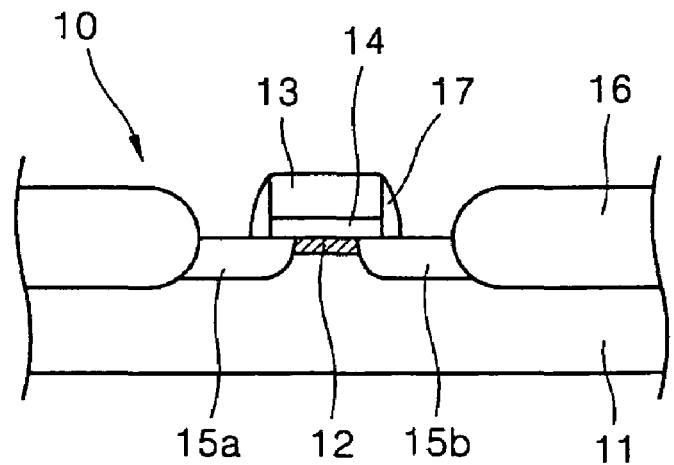
FIG. 3 is a sectional view showing the structure of a memory device including a transistor according to an embodiment of the present invention.

An example of the transistor formed by this method is shown in FIG. 3. Referring to FIG. 3, a transistor 10 has a structure where a gate electrode 13 is arranged on a conductive region 12 between a source electrode 15 and a drain electrode 15b in a silicon substrate 11, and a gate dielectric layer 14 is formed below the gate electrode 14. In the structure, the gate dielectric layer 14 is formed of a HfO$_2$ layer according to the present invention by the method as described above. Spacers 17 are formed on both sides of the gate electrode 13 and the gate dielectric layer 14 for protective purposes. In FIG. 3, reference numeral 16 denotes a non-active region.

The capacitor and/or transistor manufactured by the method according to the present invention as described above can be applied to a variety of electronic devices, for example, dynamic random access memory (DRAM) devices.

Figure 4:
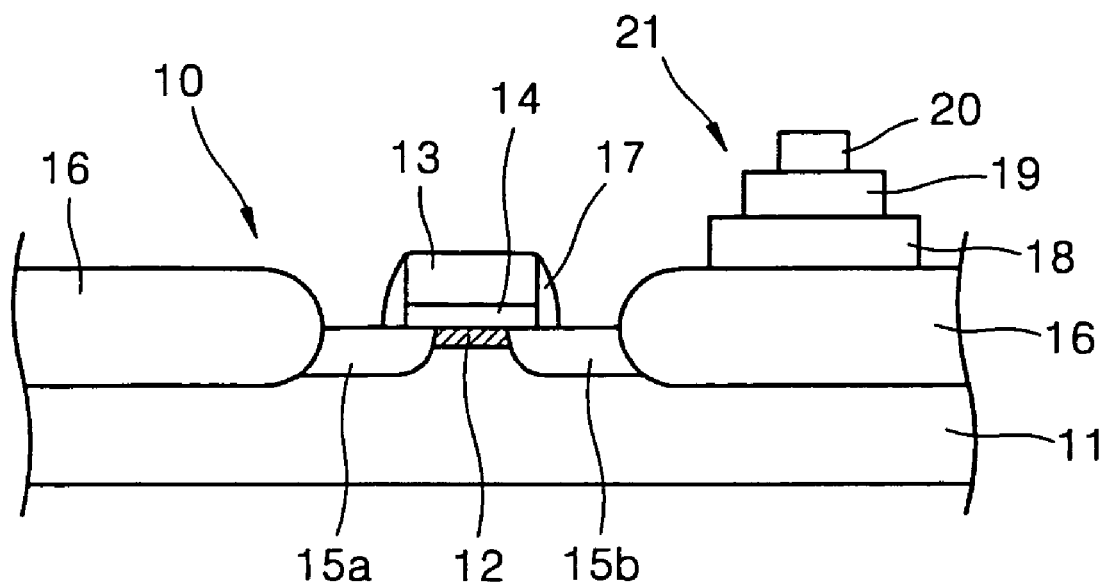
FIGS. 4 and 5 are sectional views showing the structures of memory devices, each of which includes a capacitor and a transistor, according to another embodiment of the present invention.
Figure 5:
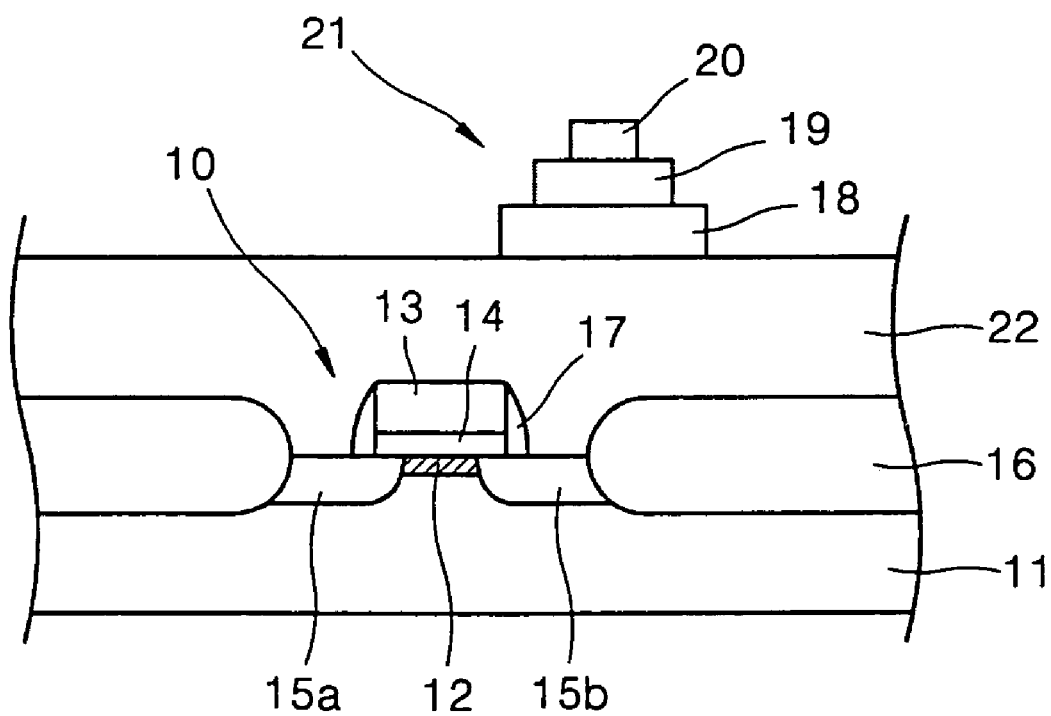

FIGS. 4 and 5 are sectional views showing the structures of memory devices using a capacitor and transistor manufactured according to the present invention. In FIGS. 4 and 5, reference numeral 10 denotes a transistor, reference numeral 11 denotes a silicon substrate, reference numeral 12 denotes a conductive region, reference numeral 13 denotes a gate electrode, reference numeral 14 denotes a gate dielectric layer, reference numeral 15a denotes a source electrode, reference numeral 15b denotes a drain electrode, reference numeral 16 denotes a non-active region, reference numeral 17 denotes a spacer, reference numeral 18 denotes a lower electrode, reference numeral 19 denotes a dielectric layer, which is formed of a hafnium oxide layer according to the present invention, reference numeral 20 denotes an upper electrode, reference numeral 21 denotes a capacitor, and reference numeral 22 denotes an underlying structure.

The present invention will be described in detail with reference to the following examples. The following examples are for illustrative purposes and are not intended to limit the scope of the invention.

EXAMPLE 1

6.406 g solid HfCl$_4$ was dissolved in 100 mL acetonitrile to obtain a 0.2-M solution. The solution was vaporized at 50° C. in a vacuum to obtain 7.254 g solid residues. The solid residues were dissolved in 100 mL tetrahydrofuran to obtain a liquid hafnium oxide precursor.

As the result of an atomic analysis using the residues, carbon and nitrogen atoms were detected in a molar ratio of 3.4:1.1. From this result, it is evident that the acetonitrile was chemically bound to the HfCl$_4$.

EXAMPLE 2

6.406 g solid HfCl$_4$ was dissolved in 100 mL pyridine to obtain a 0.2-M solution. The solution was vaporized at 50° C. in a vacuum to obtain 7.023 g solid residues. The solid residues were dissolved in 100 mL propionitrile to obtain a liquid hafnium oxide precursor.

EXAMPLE 3

6.406 g solid HfCl$_4$ was dissolved in 100 mL acetonitrile to obtain a 0.2-M solution. The solution was vaporized at 50° C. in a vacuum to obtain 7.254 g solid residues. The solid residues were dissolved in 100 mL tetrahydrofuran to obtain a liquid hafnium oxide precursor.

EXAMPLE 4

6.406 g solid HfCl$_4$ was dissolved in 100 mL acetonitrile to obtain a 0.2-M solution. The solution was vaporized at 50° C. in a vacuum to obtain 7.254 g solid residues. The solid residues were dissolved in 100 mL acetonitrile to obtain a liquid hafnium oxide precursor.

EXAMPLE 5

The liquid hafnium oxide precursor obtained in Example 3 was sprayed through a nozzle into a vaporizer for ALD, and the produced aerozole was vaporized. Here, the liquid hafnium oxide layer precursor was provided for 0.01 seconds by time division synchronization. The precursor vapor was transferred into a reactor while a carrier gas was flowed into the same at 200 sccm, and adsorbed on a Poly-Si/SiO$_2$/Si substrate. Here, the reactor was maintained at 200° C. and 0.17 torr. The unreacted precursor was removed from the reactor by flowing nitrogen gas at 200 sccm for 3 seconds. Water vapor was injected into the reactor as an oxidizing agent for 3 seconds at room temperature and under the pressure generated by the vapor in order to oxidize the adsorbed precursor and form a HfO$_2$ layer. The reactor was purged again with nitrogen gas at 200 sccm. Next, the above processes were repeated until a HfO$_2$ layer having a desired thickness was deposited.

Figure 6:
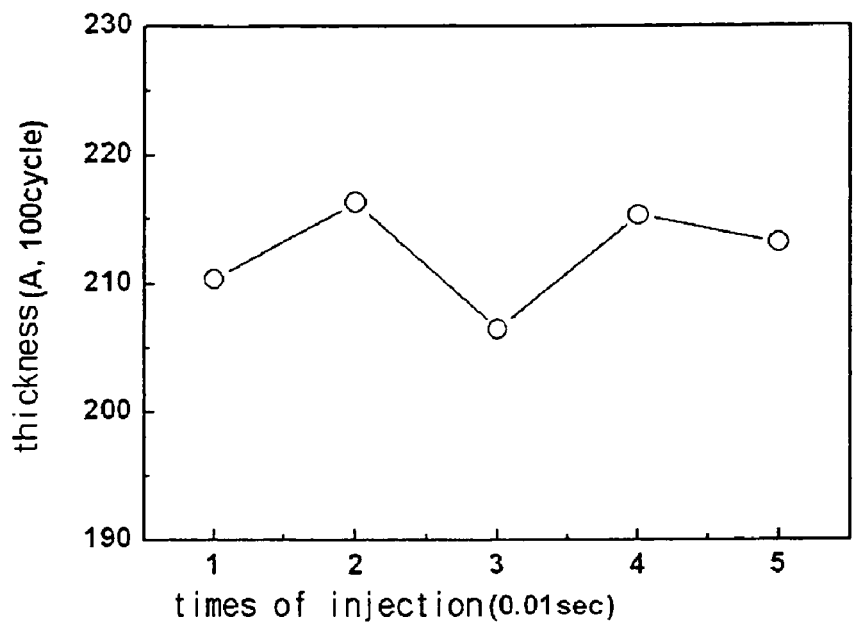
FIG. 6 is a graph for illustrating thickness variations of a hafnium oxide layer with respect to the number of times the hafnium oxide precursor according to the present invention is supplied.

In an experiment, the amount of injection of the precursor was increased by increasing the number of times the precursor was pulsed. The result is shown in FIG. 6. As is apparent in FIG. 6, even when the increased amounts of the precursor were injected, the deposition rate of the precursor remained consistent, satisfying the requirement of ALD.

Figure 7:
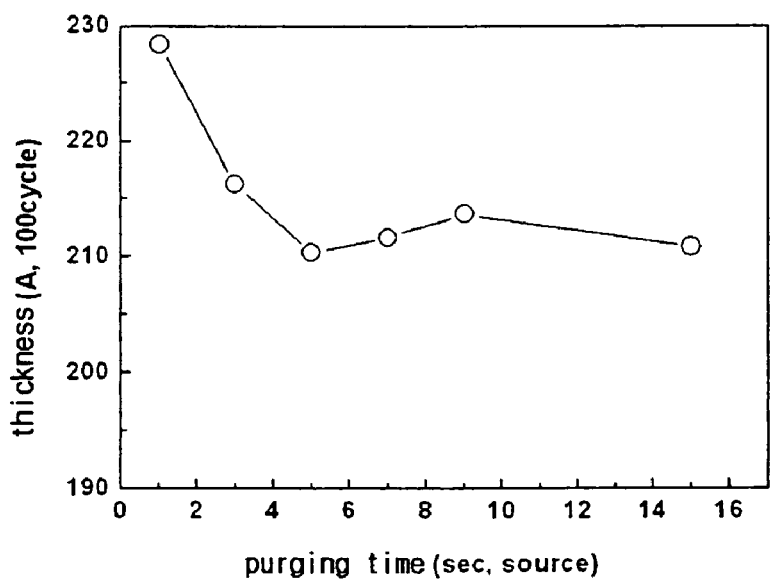
FIG. 7 is a graph for illustrating thickness variations of a hafnium oxide layer with respect to the purging time of an inert gas.

FIG. 7 is a graph of deposition rate with respect to purging time. When the precursor was purged for 3 seconds or longer, no reaction between the precursor and the water vapor supplied as the oxidizing agent occurred since there is not the contact between the precursor and the water vapor. The deposition rate of the pure precursor was 0.2 nm/cycles or greater.

EXAMPLE 6

A $HfO_2$ layer was formed in the same manner as in Example 5, except that the liquid hafnium oxide precursor prepared in Example 2, instead of that prepared in Example 3, was used. The concentrations of impurities in the $HfO_2$ layer were measured. The results are shown in FIGS. 8 and 9.

Figure 8:
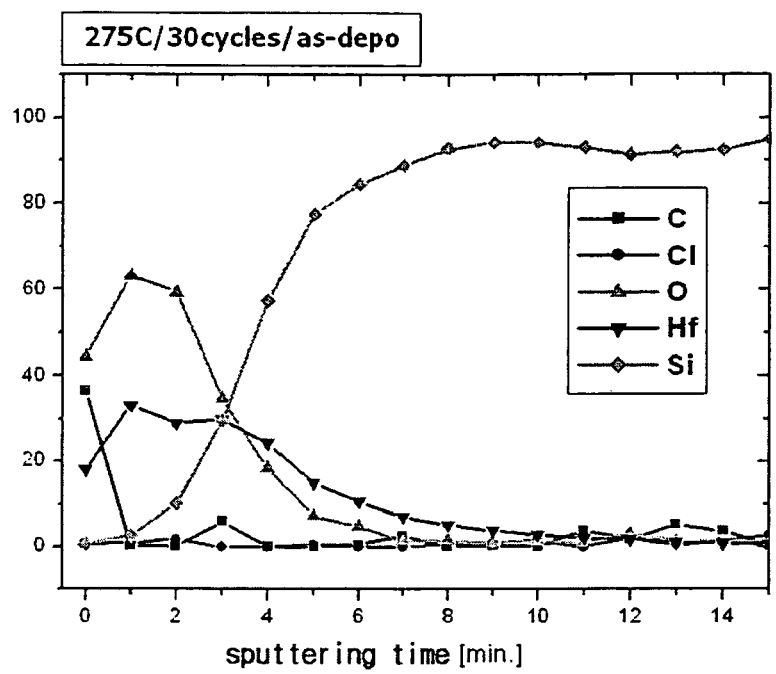
FIGS. 8 and 9 illustrate the concentrations of impurities in hafnium oxide layers formed by a method according to the present invention.
Figure 9:
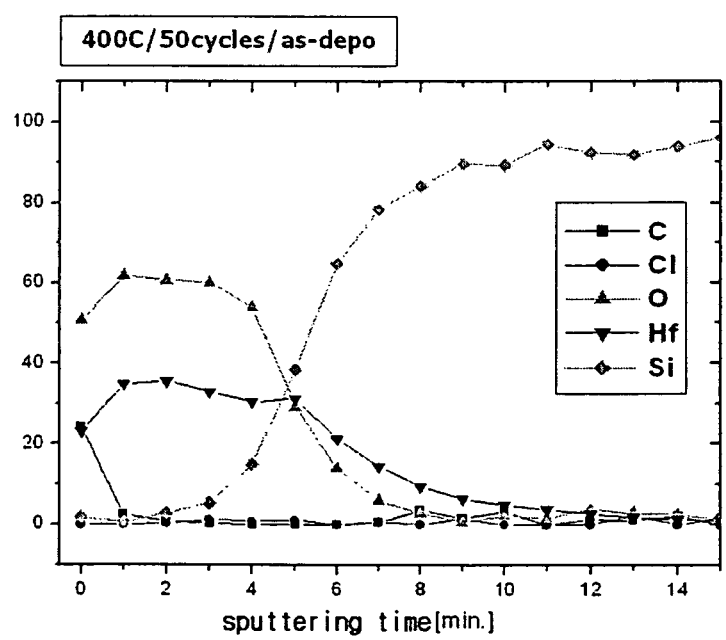

As shown in FIGS. 8 and 9, at a deposition temperature of 270 and 400° C., respectively, chlorine and carbon were detected at less than 1% each. Evidently, a quality $HfO_2$ layer can be formed using the precursor according to the present invention. The deposition rate was 0.2 nm/cycles or greater as in Example 5.

EXAMPLE 7

A $HfO_2$ layer was formed in the same manner as in Example 5, except that the liquid hafnium oxide precursor prepared in Example 4, instead of that prepared in Example 3, was used. Step coverage was measured using the $HfO_2$ layer. The result is shown in FIG. 10.

Figure 10:
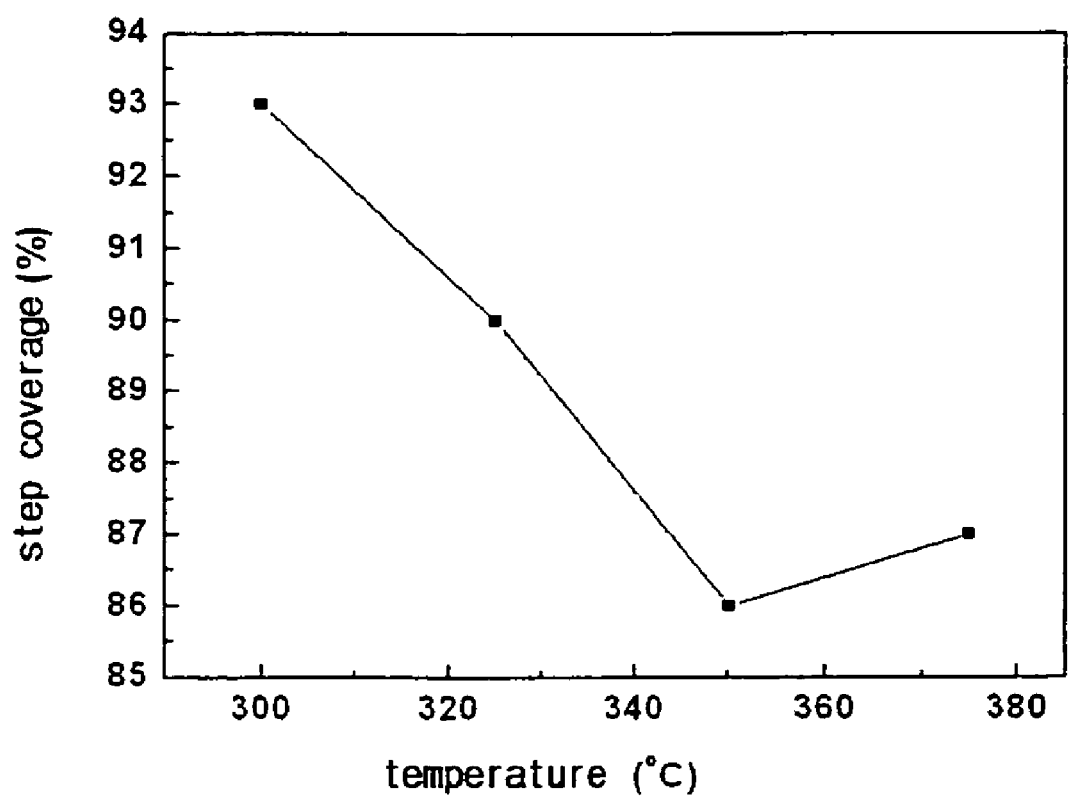
FIG. 10 illustrates the step coverage of a hafnium oxide layer according to the present invention.

As is apparent from FIG. 10, when the $HfO_2$ layer was formed by spraying the liquid precursor through a nozzle according to the present invention, the step coverage was improved up to 85% or greater, compared to a conventional bubbling method achieving 30% or less step coverage.

EXAMPLE 8

A $HfO_2$ layer was formed on a poly-$Si/SiO_2/Si$ substrate at 300° C. using the liquid hafnium oxide precursor prepared in Example 4, followed by annealing at 750° C. for 10 minutes in the air. A Pt electrode was formed on the $HfO_2$ layer by sputtering, and the electrical characteristics were measured. As a result, an electrical characteristic of $10^{-7}$ $A/cm^2$ or less at 1 V, which is the requirement of electronic devices, was obtained.

As described above, the present invention provides a hafnium oxide precursor which can be deposited at a low temperature and a high rate and provides improved electrical characteristics and step coverage. The present invention provides a method for forming a hafnium oxide layer using the precursor, a capacitor or a transistor that include a hafnium oxide layer formed by the method, and electronic devices including the capacitor and/or transistor.

While the present invention has been particularly shown and described with reference to preferred embodiments thereof, it will be understood by those of ordinary skill in the art that various changes in form and details may be made therein without departing from the spirit and scope of the present invention as defined by the appended claims.

What is claimed is:

1. A method for forming a hafnium oxide layer, comprising:
   preparing a solution of a hafnium oxide precursor containing a nitrogen compound bound to $HfCl_4$;
   adsorbing the hafnium oxide precursor solution onto a surface of a substrate in a reactor; and
   oxidizing the product adsorbed on the surface of the substrate by supplying an oxidizing agent into the reactor, to form an atomic hafnium oxide layer on the substrate.

2. The method of claim 1, further comprising supplying a reaction activator before or after supplying the oxidizing agent, or simultaneously.

3. The method of claim 1, wherein the oxidizing agent is water vapor, $O_2$ gas, $N_2O$ gas, or plasma-enhanced $O_2$ or $O_3$ gas.

4. The method of claim 2, wherein the reactor activator includes pyridines, acetonitriles, and amines.

5. The method of claim 1, wherein the hafnium oxide precursor solution contains at least one organic solvent selected from the group consisting of tetrahydrofuran, n-butylacerate, cyclohexane, propionitrile, and butyronitrile.

6. The method of claim 1, wherein the hafnium oxide precursor solution is supplied into the reactor via a vaporizer.

7. The method of claim 1, wherein the hafnium oxide precursor solution is supplied under time-division synchronization by opening and closing a nozzle of the vaporizer.

* * * * *